United States Patent [19]

Stone et al.

[11] 4,315,892

[45] Feb. 16, 1982

[54] FLUID COLLECTION DEVICE HAVING PHASE PARTITIONING MEANS

[75] Inventors: Glen Stone, O'Fallon; Gary J. Haglund, Creve Coeur, both of Mo.

[73] Assignee: Sherwood Medical Industries, Inc., St. Louis, Mo.

[21] Appl. No.: 170,222

[22] Filed: Jul. 18, 1980

[51] Int. Cl.³ .................... G01N 33/48; B01D 21/26
[52] U.S. Cl. .................................... 422/101; 210/361; 210/782; 210/927; 210/DIG. 24; 422/102
[58] Field of Search .......... 422/102, 101, 72; 128/760; 233/1 R, 26; 210/360.1, 361, 782, DIG. 24, 927; 23/230 B

[56] References Cited

U.S. PATENT DOCUMENTS

| 3,647,070 | 3/1972 | Adler | 210/361 X |
|---|---|---|---|
| 3,846,077 | 11/1974 | Ohringer | 422/101 X |
| 3,957,653 | 5/1976 | Blecher | 210/927 X |
| 3,976,579 | 8/1976 | Bennett | 233/26 X |
| 4,055,501 | 10/1977 | Cornell | 210/927 X |
| 4,088,582 | 5/1978 | Murty et al. | 210/927 X |
| 4,152,270 | 5/1979 | Cornell | 210/927 X |
| 4,180,465 | 12/1979 | Murty | 210/927 X |
| 4,189,382 | 2/1980 | Zine, Jr. | 210/782 X |
| 4,235,725 | 11/1980 | Semersky | 210/927 X |
| 4,246,123 | 1/1981 | Cornell | 210/782 |

Primary Examiner—Ronald Serwin
Attorney, Agent, or Firm—Stanley N. Garber; William R. O'Meara

[57] ABSTRACT

A fluid collection device for collecting and separating a liquid into its phases is provided which includes a collection container and an elongate housing having gel-like sealant therein. The sealant has a specific gravity between those of the separated low and high density phases. The housing has a sealant flow control valve in the low density phase portion of the container which is opened in response to a decrease in the specific gravity of the liquid adjacent the valve.

19 Claims, 4 Drawing Figures

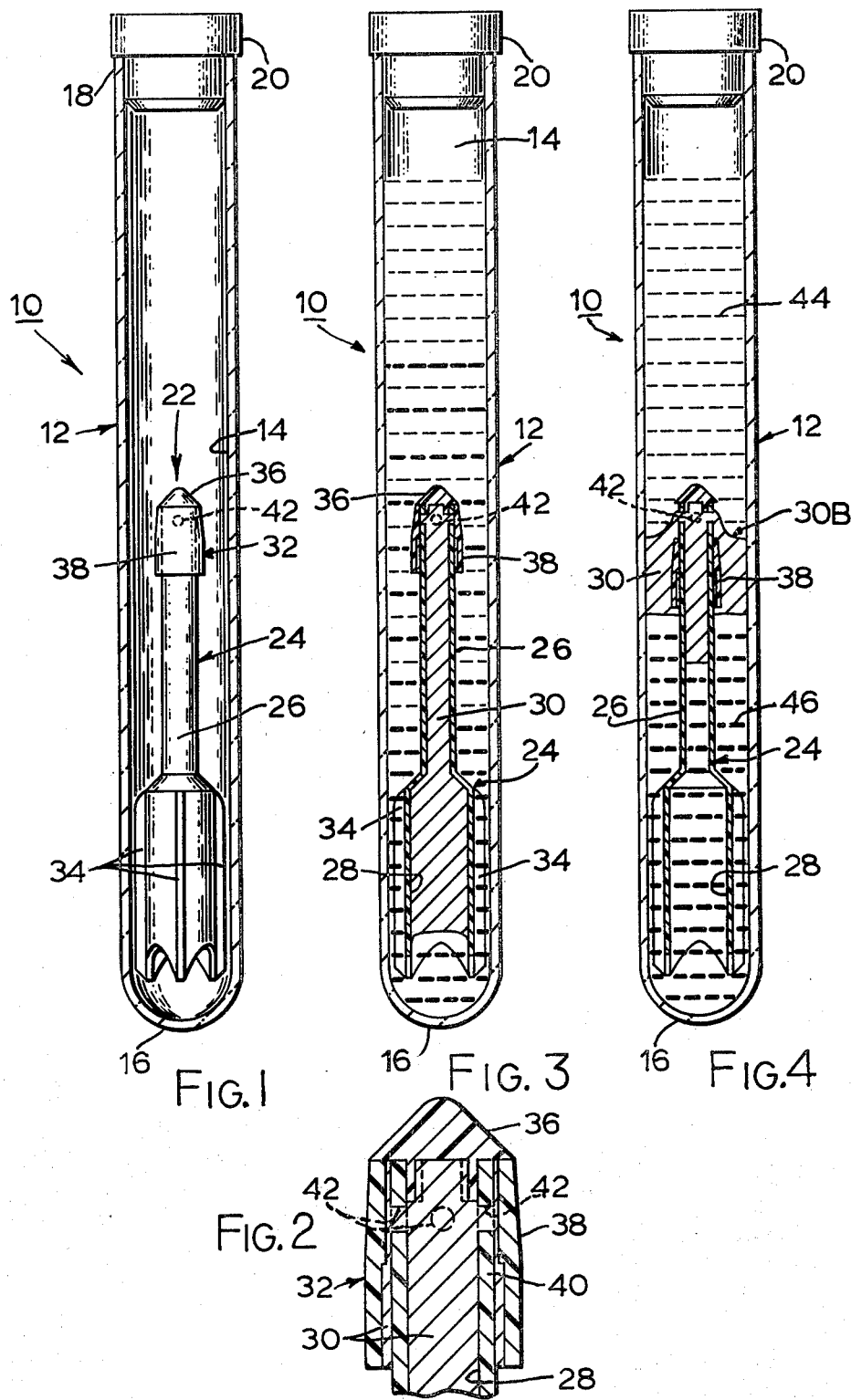

FLUID COLLECTION DEVICE HAVING PHASE PARTITIONING MEANS

TECHNICAL FIELD

This invention relates to fluid collection devices having phase partitioning means and more particularly to an improved fluid collection device utilizing a phase partitioning gel-like material for providing a phase partition during centrifugation of the device.

BACKGROUND ART

When taking blood samples for test purposes, whole blood is generally drawn into an evacuated fluid or blood collection container or tube, and the tube is subsequently centrifuged to separate the blood into its major phases, that is, its relatively light or low density phase, serum or plasma, and its heavy or high density cellular phase. Blood phase separators or partitioning devices have been used to provide a partition or barrier between the separated phases until the light phase is removed for clinical testing. Some proposed partitioning arrangements include the use of a sealant or a gel-like material having a specific gravity intermediate the specific gravities of the light and heavy blood phases so that during centrifugation and phase separation, the sealant automatically flows to the interface of the two phases and forms a semi-solid partition between them. Various gel-like materials or sealants are now well known. For example, in U.S. Pat. No. 3,852,194, a thixotropic, gel-like mixture of silicone and hydrophobic silicon dioxide powders is used to form a partition between separated phases. In U.S. Pat. Nos. 4,021,340; 4,088,582 and 4,055,501, mixtures including a liquid polybutene polymer and silicon dioxide powders are used as gel-like phase partitioning materials.

There are certain problems associated with the use of gel-like sealants as phase barriers. In some cases, there is the possibility that the sealant will form a barrier too early so that red cells are trapped in the light phase, serum or plasma, thereby causing contamination of the light phase and inaccurate clinical test results. In some constructions, the sealant travels through the heavy cellular phase colliding with cells, and this is believed to cause cell hemolysis which adds to the contamination of the light phase. On the other hand, in some cases, there is the possibility that the sealant will not flow soon enough after centrifugation has been initiated or that it will remain in its initial location and fail to form a barrier or an adequate one. In general, because of variations in temperature and sealant viscosity, speed of the centrifuge, sealant aging, and other factors, the use of gel-like sealant materials as phase partitions have not been entirely reliable.

In copending applications, U.S. Ser. Nos. 31,816 now abandoned, 31,817, now abandoned and 31,818, filed Apr. 20, 1979, now U.S. Pat. No. 4,246,123, and which have the same assignee as this application, standpipes are disclosed for conveying sealant through the high density phase for reducing red cell hemolysis and also to meter the flow of gel through the pipe so that it does not reach the interface too early. While these devices are improvements, the flow characteristics of the sealant through the standpipes may still vary due to one or more of the above-mentioned possible variations.

DISCLOSURE OF THE INVENTION

Accordingly, it is an object of the present invention to provide a fluid collection device having partitioning means for forming an improved partition between separated low and high density phases of a multi-phase liquid, such as whole blood, during centrifugation, while obtaining more reliable and desirable sealant flow characteristics. A more specific object is to provide a blood phase separation device which minimizes hemolysis of blood during centrifugation, reduces the amount or prevents blood cells remaining in the low density phase, and tends to provide a reliable and desirable phase partitioning device after centrifugation. In accordance with one aspect of the present invention, these objects are obtained by providing a liquid container for receiving a liquid to be centrifugally separated into relatively low and high density phases, and a phase partitioning device disposed in the container which includes a housing having gel-like sealant therein, and valve means responsive to a predetermined degree of phase separation to initiate the flow of sealant from the housing so as to form a partition between the separated phases during centrifugation.

These, as well as other objects and advantages of the present invention, will become apparent from the following detailed description and drawing.

BRIEF DESCRIPTION OF THE DRAWING

FIG. 1 is an elevational view in cross-section of a fluid collection device in accordance with a preferred embodiment of the present invention;

FIG. 2 is an enlarged elevational view in cross-section of the upper end portion of the phase partitioning device of the collection device of FIG. 1;

FIG. 3 illustrates the fluid collection device of FIG. 1 during an initial stage of centrifugation; and FIG. 4 illustrates the fluid collection device of FIG. 1 after complete phase separation and centrifugation.

DESCRIPTION OF A PREFERRED EMBODIMENT

Referring now to the drawing, and particularly to FIGS. 1–3, there is shown a fluid collection device illustrated as a blood collection device 10 adapted to receive a sample of whole blood. The device 10 includes a blood collection container or tube 12, for example of glass, which has a blood collection chamber 14 closed at the bottom by an integral container end portion 16. Container 12 has an open end 18 that is closed by a stopper 20. Disposed in chamber 14 of the collection container 12 is a fluid or blood phase partitioning device indicated generally at 22.

The stopper 20 may be a conventional rubber stopper which is pierceable by a needle cannnula for introducing blood into chamber 14 and which is self-sealing at the site of penetration when the needle is removed from the stopper. Preferably, the chamber 14, during manufacture of the device 10, is provided with a predetermined negative pressure or vacuum with the stopper maintaining the negative pressure in the chamber until the device is used.

The phase partitioning device 22 includes a housing 24 shown as an elongate hollow partition member having a central, generally cylindrical standpipe or tubular portion 26 that has an inner sealant chamber 28 (FIG. 3) filled with a gel-like partitioning or barrier forming sealant material 30, and a phase separation responsive sealant flow control valve indicated generally at 32. The housing 24 is generally "rocket" shaped and has three guide ribs or wings 34 at the lower end which extend radially outwardly from tubular portion 26 and frictionally engage the inner sidewall of the container 12 adjacent the lower end of the container to center and hold the device 22 in place. The chamber 28 is open at the bottom and closed at the top by a closure cap 36 which may be cemented to the upper end of the housing. The ribs 34 also hold the device 22 spaced from the bottom 16 of the container. The housing 24 and its chamber 28 extend upwardly into that portion of the container 12 or chamber 14 which contains the separated low density phase, serum or plasma, after complete phase separation. The valve 32, as best seen in FIG. 2, includes a relatively movable valve member 38 and an upper portion 40 of the tubular housing portion 26, which portion 40 has a sealant outlet illustrated in the form of four circumferentially spaced outlet openings 42 extending through the sidewall of the valve portion 40.

The valve 32 is shown in FIGS. 1-3 in the normally closed position, that is, with the valve member 38 surrounding and closing the sealant outlet openings 42. In the closed position, no sealant 30 can flow out of the housing 24 and into the liquid in the container 12. One way to keep the valve member 38 at the upper end of housing 24 and in its normally valve closed position is to apply sealant material 30, as seen in FIG. 2, between the inner surface of valve member 38 and the outer surface of valve portion 40. This sealant serves somewhat as an adhesive to hold the valve member 38 in its closed position during normal handling and until device 10 is used. During phase separation and centrifugation of device 10, the sealant on the inner surface of member 38 acts somewhat as a lubricant allowing the valve member 38 to readily move relative to the valve portion 40 to open the valve 32. Upward movement of the valve member 38 is limited by its engagement with the bottom of cap 36. The cap 36 may be applied to the upper end of housing 24 after the movable valve member 38 has been placed onto the upper end of housing 24. The sealant 30 may be a thixotropic gel-like material that is substantially water insoluable and inert to the components of blood, and has a specific gravity intermediate the specific gravities of the separated light phase, which is about 1.03, and the heavier cellular phase which is about 1.09. The sealant is generally formed so as to have a specific gravity between about 1.035 and 1.06 and preferably has a specific gravity about 1.04 or 1.045. The sealant 30 at rest and under normal handling and shipping conditions is semi-solid or non-flowable, but when subjected to forces such as centrifugal forces occurring during separation of the blood phases, it becomes flowable. Upon cessation of the centrifugal forces, the sealant returns to its semi-solid or substantially non-flowable state.

As previously mentioned herein, the sealant material 30 may be, for example, a mixture of silicone and hydrophobic silicon dioxide powders or a mixture of polybutene polymer and silicon dioxide powder. One specific example of a useful sealant is described in U.S. Pat. No. 4,088,582 and includes one-hundred parts by weight of polybutene (Polybutene Grade 24—Chevron Chemical Company, San Francisco, Calif.), twenty parts by weight of hydrophillic silica powder (Min-U-Sil 10, PGS, a subsidiary of ITT, Pittsburgh, Pa.), and nine parts by weight of a hydrophobic silica powder (Aerosil R-972, Degussa Inc., Pigments Division, New York, N.Y.). The latter silica powder may be made hydrophobic by a process including flame hydrolysis of silica, and then reacting the silica with dimethyl dichlorosilane and steam in a fluidized bed reactor heated to about 400° C. by means of an inert gas. By varying the proportions of polybutene and silica powders, desired viscosity and specific gravity characteristics can be obtained.

The specific gravity of the valve member 38 is made so that it is between the specific gravity of whole blood, which is about 1.05, and may be in a range of about 1.048 to 1.066, and the specific gravity of the low density blood phase which is about 1.03, and may be in the range of about 1.026 to 1.031. Preferably, the specific gravity of the valve member 38 is made to be about 1.04 which is below that of whole blood and higher than that of the low density phase for purposes explained hereafter.

In use, a sample of blood may be drawn into the chamber 14 of container 12 by using a double-ended needle cannula such as provided by a conventional needle holder and tube guide. For example, after the distal end of the cannula is inserted into the vein of a patient, the device 10 is moved onto the proximal end of the cannula until the cannula pierces stopper 20, whereupon whole blood flows into container 12. The filled container is subsequently placed in a centrifuge such that the lower end 16 will be radially outwardly of the stopper 20 and the axis of rotation of the centrifuge during centrifugation. As is well known, if it is desired to separate serum, a blood clot is formed before centrifuging the device. On the other hand, where plasma is desired, an anticoagulant may be placed in the tube during manufacture to prevent clotting.

In FIG. 3, the container 12 is illustrated as having been filled with a whole blood sample and as having been subjected to an initial amount of centrifugation. During centrifugation of device 10, the blood cells or clot and other components of the heavier or higher density cellular phase begin downward movement toward the lower end 16 of the container 12, while the light or lower density phase components move upwardly or toward the upper end 18. The components of the higher density phase move by the ribs 34 and into the lower end of housing chamber 28 urging the sealant material 30 upwardly in the chamber. As centrifugation of device 10 continues, there will be a changing specific gravity gradient along the column of blood. In FIG. 3, the upper portion, indicated by thin dashed lines, becomes substantially free of red blood cells and contains mainly the light phase, and has a relatively low specific gravity, for example 1.035. At the bottom of container 12, a portion of the blood is indicated by heavy dashed lines and represents a relatively high concentration of cellular phase components including red blood cells, and this portion will have a relatively high specific gravity, for example 1.08. A center portion of the blood, indicated by alternate light and heavy dashed lines, represents a mixture of cellular phase components including blood cells, and light phase, plasma or serum, and its specific gravity will be between that of the upper and lower portions, for example, 1.05. Upon complete phase separation, as indicated in FIG. 4, the blood will, of course, be divided into its two major phases, the low-density phase, plasma or serum 44, in the upper or light phase zone or portion of the container, and the high-density or cellular phase 46 at the bottom of the container or in the heavy phase zone or portion of the container.

As illustrated in FIG. 3, the blood portion adjacent the valve 32 has a specific gravity (e.g., 105) that is greater than that of the valve member 38 (1.04) so that the valve 32 is still in its closed condition. As the specific gravity of the blood portion about the valve 32 decreases to a value below 1.04, for example, to 1.035 or 1.03, the valve member 38 begins to sink or move downwardly under the centrifugal forces and away from the outlet openings 42. In this way, the valve 32 is actuated to the open position in response to a predetermined or desired specific gravity of the liquid or blood portion adjacent the valve member 38 and is therefore responsive to a predetermined or selected degree of phase separation to open and allow sealant to flow into the blood.

Once the valve 32 has opened or the valve member 38 has unblocked the sealant outlet openings 42, the centrifugal forces acting on the bottom of the column of sealant in chamber 28 by the cellular phase components causes the sealant to move upwardly in chamber 28 and out the openings 42. Since the sealant material has a specific gravity intermediate the two phases (e.g., 1.045), it seeks the interface between the separated phases. Since a desired degree of phase separation has occurred before the valve member 38 moves down to open the sealant outlet openings 42, the sealant begins moving through blood portions that have been cleared or partially cleared of blood cells. The sealant 30 moves radially outwardly and eventually slightly downwardly toward the interface, since the outlet openings 42 are in the light phase zone of the container (above the final interface). In this way, the sealant 30 tends to form a barrier, indicated at 30B, FIG. 4, from the bottom so that any late settling cells will be covered by the downwardly moving sealant as the barrier is fully formed to thereby further insure that the separated final light phase is substantially free of cells.

The sealant 30, after complete phase separation, forms the barrier 30B transversely across the container chamber 14, as shown in FIG. 4. The sealant 30 is shown filling the upper portion of housing 24, the inlet openings 42, and the space between the housing portion 40 and valve member 38, and it contacts the sidewall of the container 12. The valve member 38 is disposed in the sealant 30 of the barrier 30B since its specific gravity is intermediate those of the light and heavy phases. The barrier 30B, in the interface zone, provides a semi-solid seal between the separated low and high density blood phases 44 and 46 which can withstand normal handling and storage prior to removal of the light phase for test purposes.

Since the valve 32 is actuated to the open position in response to a selected or predetermined specific gravity of liquid adjacent the valve member 38, the time that valve 32 delays the flow of sealant 30 is substantially independent of the time it takes the liquid to reach the selected specific gravity or reach the selected degree of phase separation. Thus, good flow characteristics can be obtained even where centrifuges are operated at different speeds in the various laboratories. The actuation of the valve 32 is also substantially independent of temperature and sealant viscosity since it is actuated in response to the specific gravity of the liquid or blood in which it is disposed. Also, the housing 24 conveys sealant 30 upwardly through the cellular phase zone of the container without the sealant colliding with downwardly moving blood cells, and this tends to reduce cell hemolysis and the carrying of cells to the interface which may otherwise occur where no housing is employed.

If desired, the cylindrical sleeve valve member 38, in some cases, may be initially located below the outlet openings. Since the specific gravity of member 38 (e.g., 1.04) is below that of whole blood (about 1.05), the member 38 will tend, at first, to rise when whole blood is introduced into the container, and close the outlet openings 42. After the specific gravity of the blood adjacent valve member 38 falls below that of the member 38 during centrifugation, the member 38 will move down and allow sealant to flow toward the phase interface.

Instead of using sealant between the valve member 38 and the housing 24 as in FIG. 2, the valve member may be sized to provided a slight friction fit which holds member 38 in place until centrifugally moved.

The housing 14 may be made out of any suitable material, for example, a plastic such as polypropylene. The valve member 38 may be made from a suitable material such as a plastic, for example, a polystyrene having the desired specific gravity such as about 1.04. As is well known, various plastics can be mixed with fillers such as glass beads to obtain a desired specific gravity as desired or needed.

As various changes could be made in the above described construction without departing from the scope of the invention, it is intended that all matter contained in the above description and shown in the accompanying drawing be interpreted as illustrative and not in a limiting sense.

We claim:

1. A fluid collection device for receiving a liquid centrifugally separable into relatively low and high density phases and for providing a partition between the separated phases comprising a collection container for receiving the liquid to be separated, and phase partitioning means in said container including a housing, and gel-like sealant in said housing having a specific gravity between the specific gravities of the separated low and high density phases and flowable to a location between the separated phases during centrifugation to form a semi-rigid partition therebetween, and valve means on said housing responsive to a predetermined degree of phase separation during centrifugation of the device to open and allow the flow of said sealant from said housing into said liquid and toward said location between the separated phases.

2. The device of claim 1 wherein said valve means is disposed in the low density phase portion of said container, and is responsive to the specific gravity of the liquid adjacent said valve means and actuated to the valve open condition when the specific gravity of said adjacent liquid is at a predetermined value below that of the liquid when received in said container.

3. The device of claim 2 wherein said partitioning member extends substantially from the lower end of said container to a position in the low density phase portion of said container, said valve means includes a sealant outlet in said member in the low density portion of said container, and a movable valve member normally closing said outlet and responsive to a decrease in the specific gravity of the liquid in said container adjacent said valve member to a predetermined value to open said outlet and valve means.

4. The device of claim 3 wherein said valve member has a specific gravity intermediate the specific gravity of the separated low density phase and that of the liquid when received in said container.

5. The device of claim 1 wherein said partitioning member is an elongate hollow housing extending from the lower end portion of said container upwardly in the high density phase and phase interface portions and into the low density phase portion of said container, said valve means having an outlet including an opening in the sidewall of said housing in the low density portion of said container connected with said sealant for passing sealant from said housing to the partition, and said valve means includes a movable valve member normally closing said outlet including said opening and having a specific gravity intermediate that of the separated low and high density phases.

6. A blood collection device for receiving a sample of whole blood adapted to be centrifugally separated in the device into its relatively low density phase, serum or plasma, and its high density cellular phase comprising a blood collection container for receiving whole blood, and phase partitioning means in said container including a housing, gel-like sealant in said housing having a specific gravity intermediate the specific gravities of the separated high and low density phases and flowable during centrifugation of said container to a location between the separated phases to form a partition therebetween, and valve means on said housing for controlling the flow of said sealant and responsive to a decrease in the specific gravity of a portion of the blood in a part of the low density zone of said container to open and allow said sealant to flow from said housing to the location between the separated phases during centrifugation.

7. The device of claim 6 wherein said valve means is openable when the specific gravity of the blood in said part of the low density zone of said container is less than that of whole blood.

8. The device of claim 7 wherein said valve means includes a valve member having a predetermined specific gravity between that of the separated low density phase and that of whole blood and is movable to open said valve means when the specific gravity of the blood in said part of the low density zone of said container is below said predetermined specific gravity of said valve member.

9. The device of claim 7 wherein the specific gravity of said valve member is about 1.04.

10. The device of claim 6 wherein said housing includes an elongate member extending substantially from the bottom of said container upwardly through said high density and phase interface zones and into the low density phase zone, said valve means including sealant outlet means in the upper portion of said member and in said low density portion of said container, and a movable valve member in said low density portion of said container closing said outlet means, said valve member having a specific gravity between that of the separated low density phase and that of whole blood and movable to open said outlet and said valve means in response to a decrease in the specific gravity of blood in said part of the low density zone.

11. The device of claim 10 wherein said valve member has a specific gravity between about 1.03 and 1.05.

12. The device of claim 11 wherein said valve member has a specific gravity of about 1.04.

13. The device of claim 12 wherein said sealant has a specific gravity within the range of about 1.03 to about 1.05.

14. The device of claim 10 wherein said elongate member includes a generally tubular portion in the low density phase zone of said container, said tubular portion includes said outlet means which includes at least one opening in the sidewall of said tubular portion, and said movable valve member comprises an annular ring surrounding said tubular portion and normally closing said outlet means and slidable in a direction toward said high density zone of said container after the specific gravity of the blood surrounding said ring becomes less than the specific gravity of said ring to open said outlet means.

15. The device of claim 14 wherein said elongate member has radial ribs frictionally engageable with the sidewalls of said container to hold said housing in place.

16. The device of claim 3, 10 or 14 wherein said housing is open in the bottom end portion whereby the cellular phase components enter said housing displacing said sealant during centrifugation of the device.

17. The device of claim 14 wherein sealant material is disposed between said ring and the outer surface of said tubular portion to adhesively secure said ring in place until said valve means opens.

18. The device of claim 10 wherein some sealant material is disposed between the inner surface of said movable valve member and the outer surface of said elongate member so that said valve member remains in place closing said outlet means, and provides lubrication for said valve member when said valve member moves.

19. The device of claim 10 wherein both ends of said container are closed with one end closed by a needle pierceable stopper for introducing the sample of whole blood into the container with said partitioning means, and said container has a normally negative pressure therein to facilitate the introduction of whole blood through said stopper.

* * * * *